United States Patent
Meng et al.

(10) Patent No.: US 10,905,787 B2
(45) Date of Patent: Feb. 2, 2021

(54) COMBINATION SALT LAMP AND OIL DIFFUSER

(71) Applicant: Bear Down Brands, LLC, Huntington Beach, CA (US)

(72) Inventors: ShiFei Meng, Xiamen (CN); XiaoWen Zheng, Xiamen (CN); Joshua Goldberg, Huntington Beach, CA (US)

(73) Assignee: Bear Down Brands, LLC, Huntington Beach, CA (US)

( * ) Notice: Subject to any disclaimer, the term of this patent is extended or adjusted under 35 U.S.C. 154(b) by 164 days.

(21) Appl. No.: 16/102,177

(22) Filed: Aug. 13, 2018

(65) Prior Publication Data

US 2020/0046868 A1 Feb. 13, 2020

(51) Int. Cl.
*A61L 9/03* (2006.01)
*F21V 11/00* (2015.01)

(52) U.S. Cl.
CPC .......... *A61L 9/032* (2013.01); *A61L 2209/12* (2013.01); *A61L 2209/13* (2013.01); *F21V 11/00* (2013.01)

(58) Field of Classification Search
CPC .. A61L 9/032; A61L 2209/12; A61L 2209/13; F21V 11/00
See application file for complete search history.

(56) References Cited

U.S. PATENT DOCUMENTS

2013/0174842 A1* 7/2013 Young .................. A61L 9/032
128/203.14

FOREIGN PATENT DOCUMENTS

CN 106871309 A * 6/2017

OTHER PUBLICATIONS

English Translation of CN 106871309 A provided by the European Patent Office Espacenet.com: Meng Shifei; Perfuming Machine; Jun. 20, 2017 (Year: 2017).*

* cited by examiner

*Primary Examiner* — Kevin Joyner
(74) *Attorney, Agent, or Firm* — Gloria Tsui-Yip, Esq.; Gottlieb, Rackman & Reisman, P.C.

(57) ABSTRACT

A combination salt lamp and aroma/essential oil diffuser includes: a housing with an outlet for mist exiting the housing and an open space, a water tank inside the housing for storing liquid having a passageway that connects to the mist outlet and can disperse nebulized mist outwardly, a nebulizing assembly within the water tank to nebulize the liquid in the water tank, a salt crystal mineral that sits in the open space of the housing, a heating assembly with a heating element adjacent the salt crystal, a fan assembly inside the housing, and a power assembly for the nebulizing assembly, the heating assembly, and the fan assembly.

10 Claims, 11 Drawing Sheets

COMBINATION SALT LAMP AND OIL DIFFUSER

FIELD OF THE INVENTION

This invention pertains to a combination salt lamp and aroma/essential oil diffuser. In particular, a salt lamp and aroma/essential oil diffuser that effectively refreshes the ambient air.

BACKGROUND OF THE INVENTION

Existing aroma/essential oil diffusers use ultrasonic technology that produces high-frequency vibrations that turn water molecules and the dissolved plant essential oils into nanoscale mist particles of 0.1-5 microns to disperse into the air, refreshing the air with different scents.

Current models usually diffuse essential oils as its sole function, therefore some products have added extra features such as Chinese Patent No. CN 204115081 which claims a kind of oil diffuser/air freshener. This diffuser/air freshener includes the diffuser machine, essential oil tank within the diffuser machine, a negative/positive ions generator near the top of the diffuser machine, and a filter within the essential oil tank at the bottom of the diffuser machine. The negative/positive ion generator creates ozone and noise when generating negative ions. When using low power, production of negative ions is low and not effective in purifying the air. When using high power, more ozone is produced and causes health effects and the noise level increases.

Existing salt lamps use natural salt crystal minerals that passively absorb water from the air to produce negative ions to freshen the air. Such passive generation of negative ions does not produce enough negative ions to effectively refresh the air.

Therefore, there is a need for a combination salt lamp and aroma oil diffuser that can effectively refresh the ambient air.

SUMMARY OF THE INVENTION

The present invention is a combination salt lamp and aroma/essential oil diffuser. The present invention includes a heated salt crystal to produce negative ions to purify the air, with a nebulizing assembly next to the salt crystal to add humidity and fragrance from essential oil to the vicinity, increasing the production of negative ions and improving the quality and smell of the ambient air in the room.

The combination salt lamp and aroma/essential oil diffuser of the present invention includes:

a housing having an outlet for mist exiting the housing and an open space;

a water tank inside the housing for storing liquid having a passageway that connects to the mist outlet and can disperse nebulized mist outwardly;

a nebulizing assembly within the water tank to nebulize the liquid in the water tank;

a salt crystal mineral that sits in the open space of the housing;

a heating assembly with a heating element adjacent the salt crystal;

a fan assembly inside the housing; and a power assembly for the nebulizing assembly, the heating assembly, and the fan assembly.

In a first embodiment of the present invention, the open space of the housing has a mounting base, and the salt crystal mineral has an opening defining a hollow cavity that can be removably attached to the mounting base. The heating element extends into the hollow cavity of the salt crystal mineral. The salt crystal mineral may be cone shaped. The top of the salt crystal mineral may be the same or close to the same height as the mist outlet. At the opening of the salt crystal is a corresponding mounting fixture that can be connected to the mounting base. The mounting fixture can be selectively connected or disconnected from the mounting base of the housing. The mounting fixture may have locking tabs and the mounting base may have a corresponding locking groove to receive the locking thread. The mounting fixture is connected to the base by rotating the locking thread into the locking groove.

The housing of the first embodiment includes a top cover and a bottom cover. The top cover and the bottom cover lock in place to form a chamber. The fan assembly and the power assembly are both placed inside the chamber. The mounting base is on the top cover. Adjacent to the mounting base is a concave groove for receiving the water tank, which can be removably placed into the groove.

The water tank of the first embodiment includes a water container on top of a water tank base. The nebulizing assembly is an ultrasonic nebulizer assembly, which includes an ultrasonic element, male contact, and a female contact board. The ultrasonic element is positioned to be in contact with the inside of the water container. The male contact is on the water tank base and electrically connected to the ultrasonic element. The female contact board is inside the chamber. When the water tank is placed in the concave groove of the top cover, the male contact at the water tank base touches the female contact board and completes the electrical circuit.

In a second embodiment of the present invention, the housing of the second embodiment includes an upper housing and a lower housing, with each housing having a corresponding top and bottom covers forming upper and lower chambers, respectively. Upper housing is removably connected to lower housing. The open space is defined between the upper and lower housings. A bowl is placed in the open space of the housing, and a plurality of salt crystal minerals are placed in the bowl. The bowl has a central, slotted, protrusion to receive the heating assembly. The power and heating assemblies are in the lower chamber, with the water tank and fan and nebulizing assemblies in the upper chamber. The water tank is defined by a depression formed on the top cover of the upper housing. The male contact of the nebulizing assembly is on the bottom cover of the upper housing, with the female contact board on the top cover of the lower housing.

The heating assembly may include a halogen light bulb that provides both heat and light. Optionally, there is a LED light in the open space to illuminate the salt crystal. The LED light is electrically connected to the power assembly. The salt crystal mineral may be a Himalayan salt crystal mineral.

Advantages and benefits of the present invention includes:

1. Production of negative ions from heating up the salt crystal mineral. Additionally, the nebulizing assembly positioned next to the salt crystal mineral allows the mist generated to fall by gravity towards the salt crystal mineral. This, thereby, increases the production of negative ions, which in turn improves the air quality.

2. The LED or halogen light inside the salt crystal mineral filters through the salt crystal mineral to provide a warm glow. The light has several settings for different levels of brightness.

3. The removable water tank facilities cleaning. The electrical circuit to power the ultrasonic element of the water tank completes itself when the male and female contacts are in contact. This makes it easier to take apart the water tank to clean and to reassemble.

BRIEF DESCRIPTION OF THE DRAWINGS

Preferred embodiments of the present invention have been chosen for purposes of illustration and description and are shown in the accompanying drawings forming a part of the specification wherein.

DETAILED DESCRIPTION OF THE PREFERRED EMBODIMENTS

With reference to the drawings, wherein the same reference number indicates the same element throughout, there is shown in FIGS. 1 to 8 a combination salt lamp and aroma/essential oil diffuser 101 of the present invention. The combination salt lamp and aroma/essential oil diffuser 101 includes a housing 1, a water tank 2, a nebulizing assembly 3, a salt crystal mineral 4, a heating assembly 5, a fan assembly 6, and a power assembly 7.

The principle of the salt crystal mineral 4 air purification is as follow. The main composition of the salt crystal mineral 4 is sodium chloride. The salt crystal 4 absorbs water from the air, then the water evaporates, and the cycle repeats itself. In this process, negative ions are continuously produced. A heated salt crystal 4 will pull water molecules from the surrounding air to its surface, and when the water molecules interact with salt, the salt dissolves. As the water evaporates, sodium (positive ions) and ozone (negative ions) return to the neutral form, and the evaporated water molecules now carry negative ions from the ionization of the water molecules. Therefore, the air is refreshed through this continuous cycle. This unique way of producing negative ions is a special property of the salt crystal minerals 4, because of the neutral atomic structure of sodium that allows the salt crystal mineral 4 to produce negative ions in the presence of water.

Figure 1:
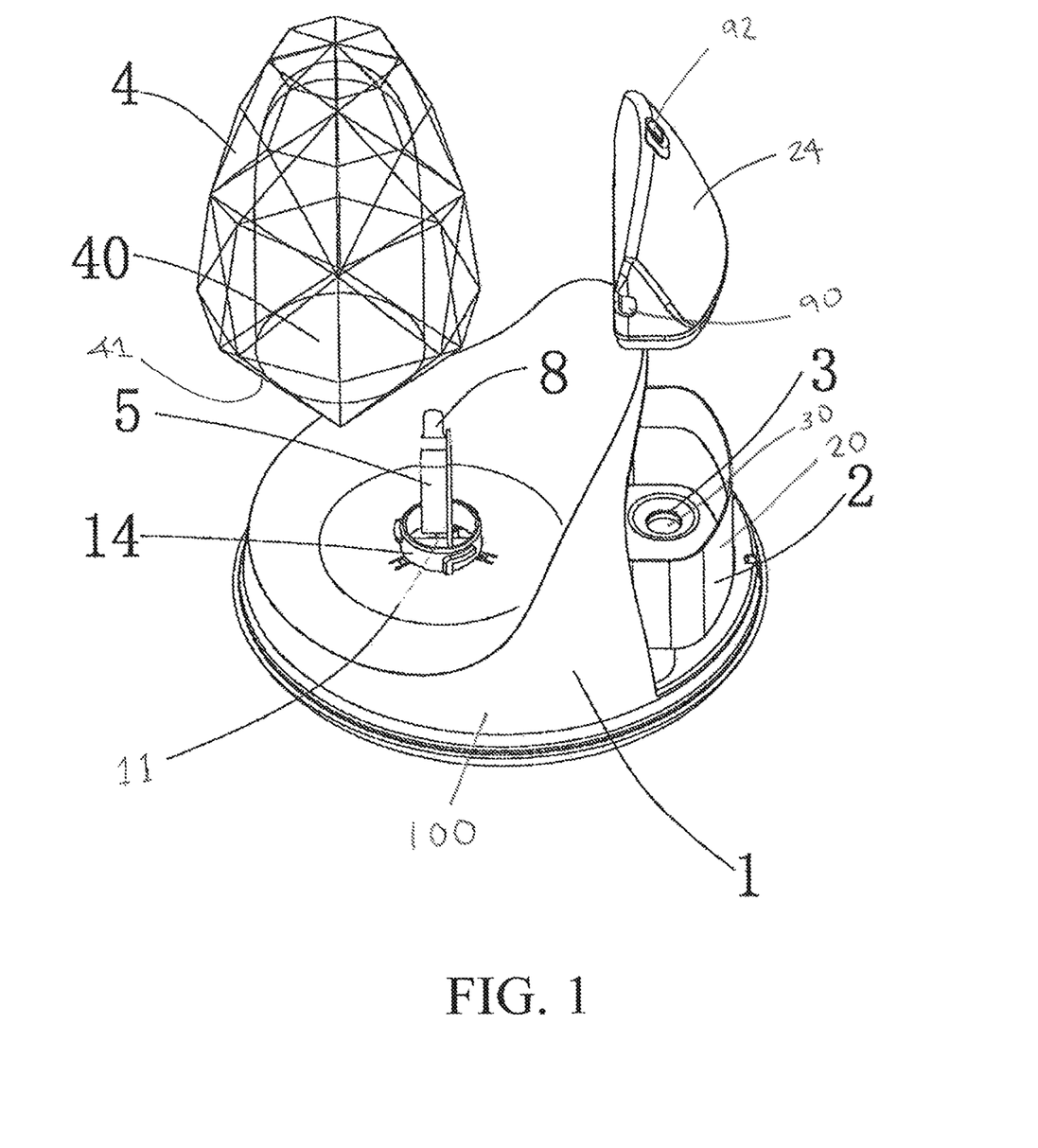
FIG. 1 is a partially exploded view of the combination salt lamp and aroma/essential oil diffuser of the present invention.
Figure 2:
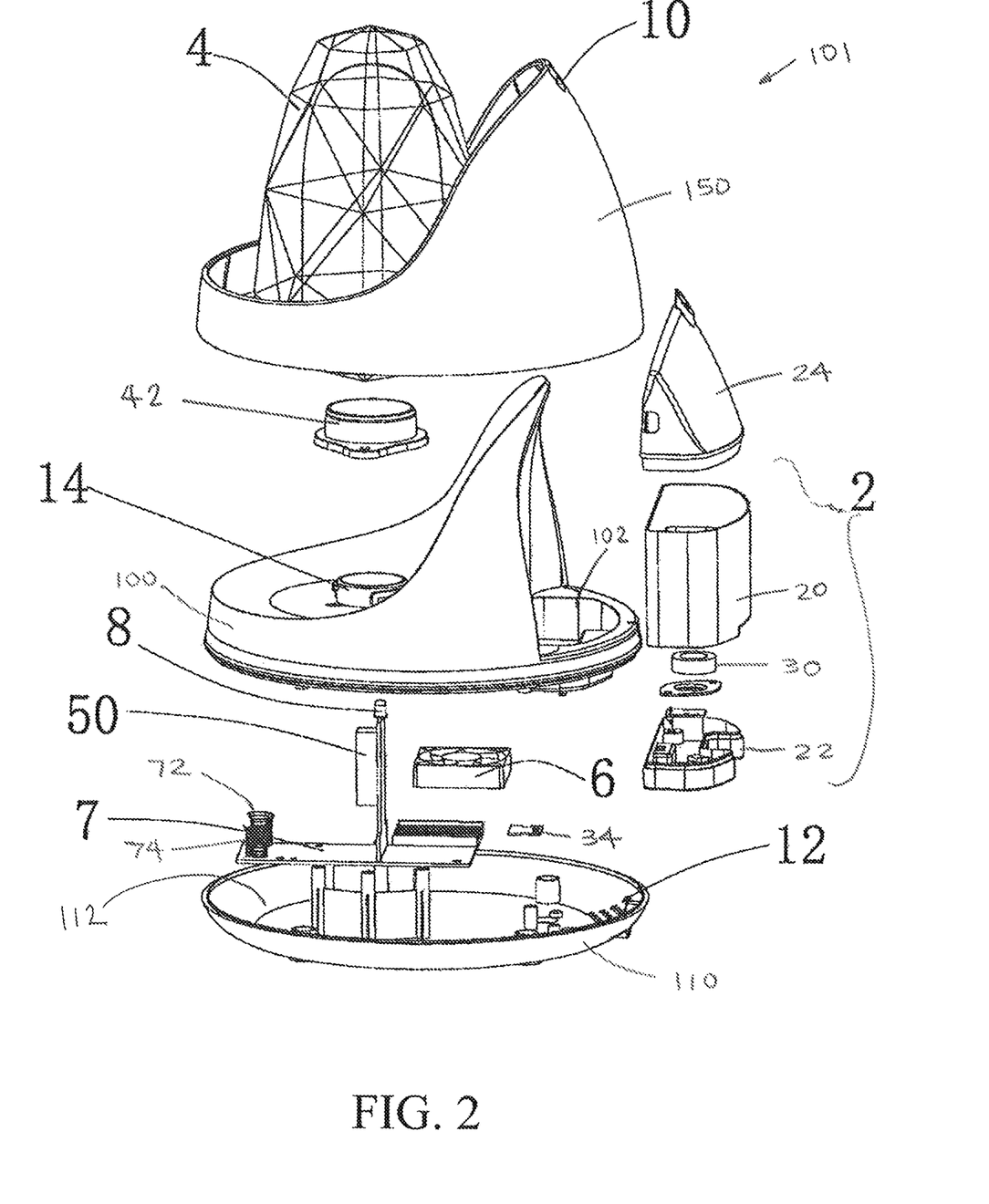
FIG. 2 is an exploded view of the combination salt lamp and aroma/essential oil diffuser of the present invention.
Figure 4:
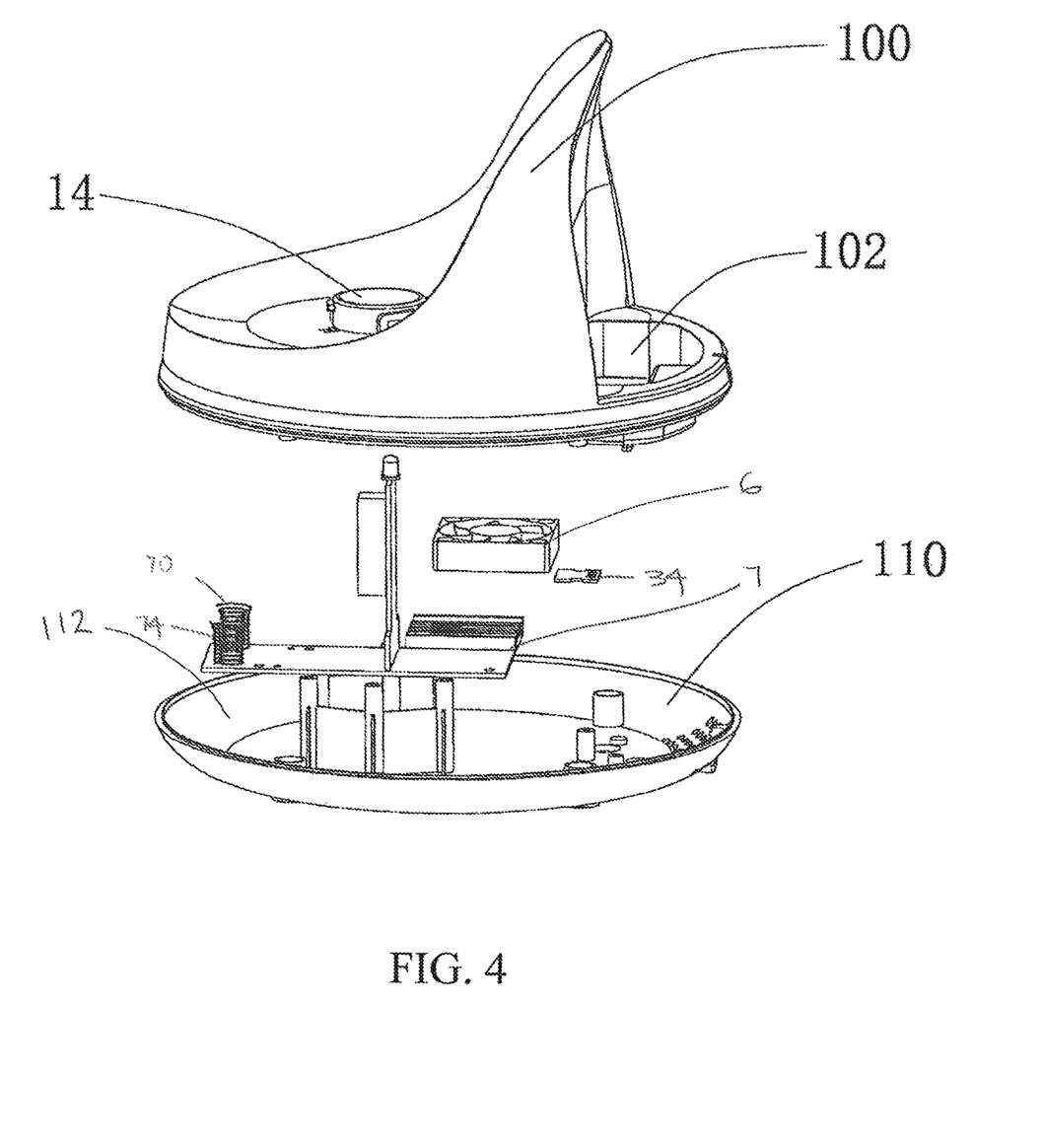
FIG. 4 is an exploded view of the housing.

The housing 1 has a mist outlet 10 and an open space 11. On the open space 11 is a mounting base 14. Housing includes a top cover 100, a bottom cover 110 and an outside cover 150. The top cover 100 and the bottom cover 110 join together to form a chamber 112. The fan assembly 6 and the power assembly 7 are both placed in chamber 112. The open space 11 and mounting base 14 are on the top cover 100. Adjacent the mounting base 14, on the top cover 100, is a concave groove 102 for receiving the water tank 2. The concave groove 102 is shaped to match the profile of the water tank 2. On the bottom cover 110 is a plurality of air inlets 12 for the intake of air from outside the diffuser 101.

Figure 5:
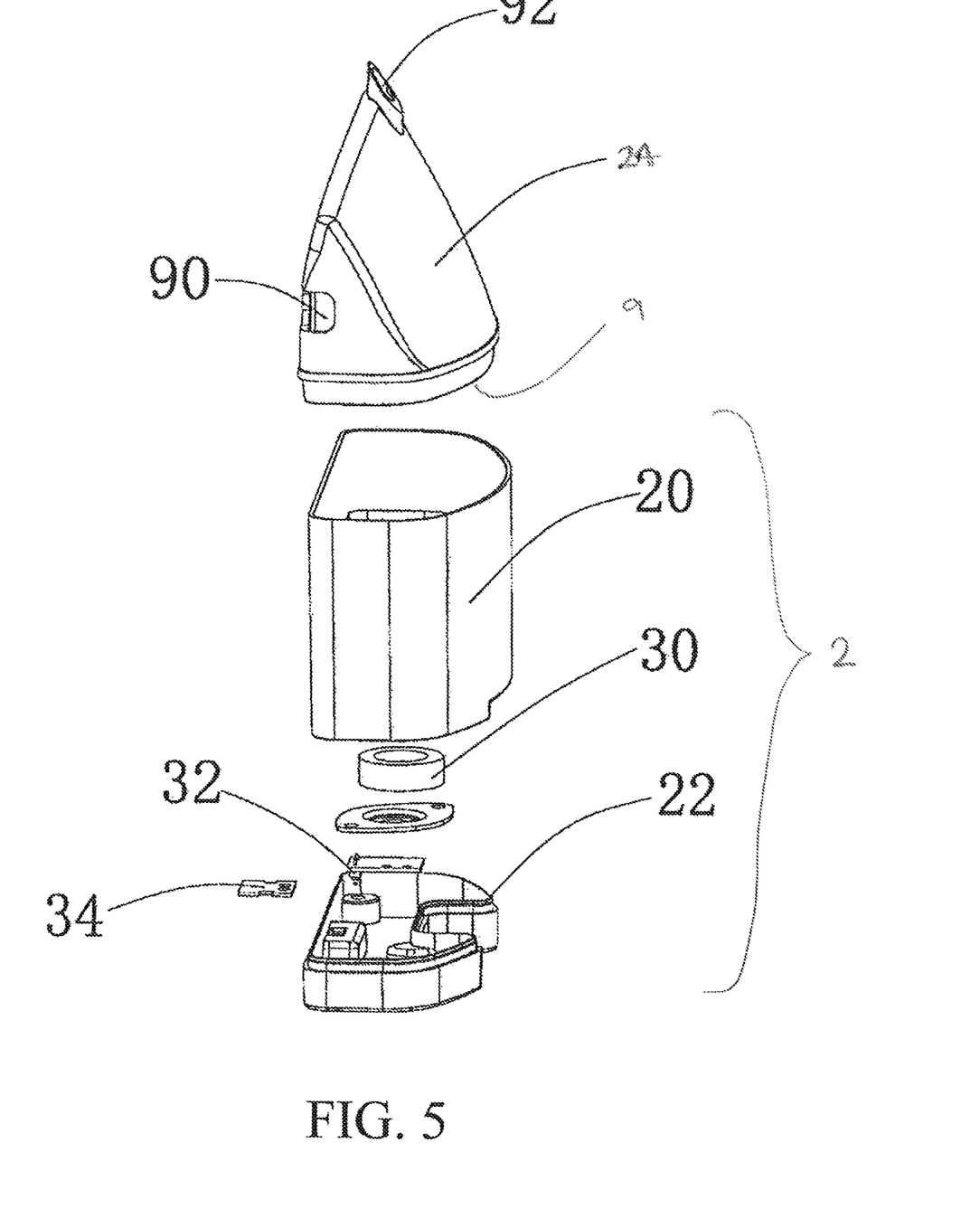
FIG. 5 is an exploded view of the water tank.
Figure 6:
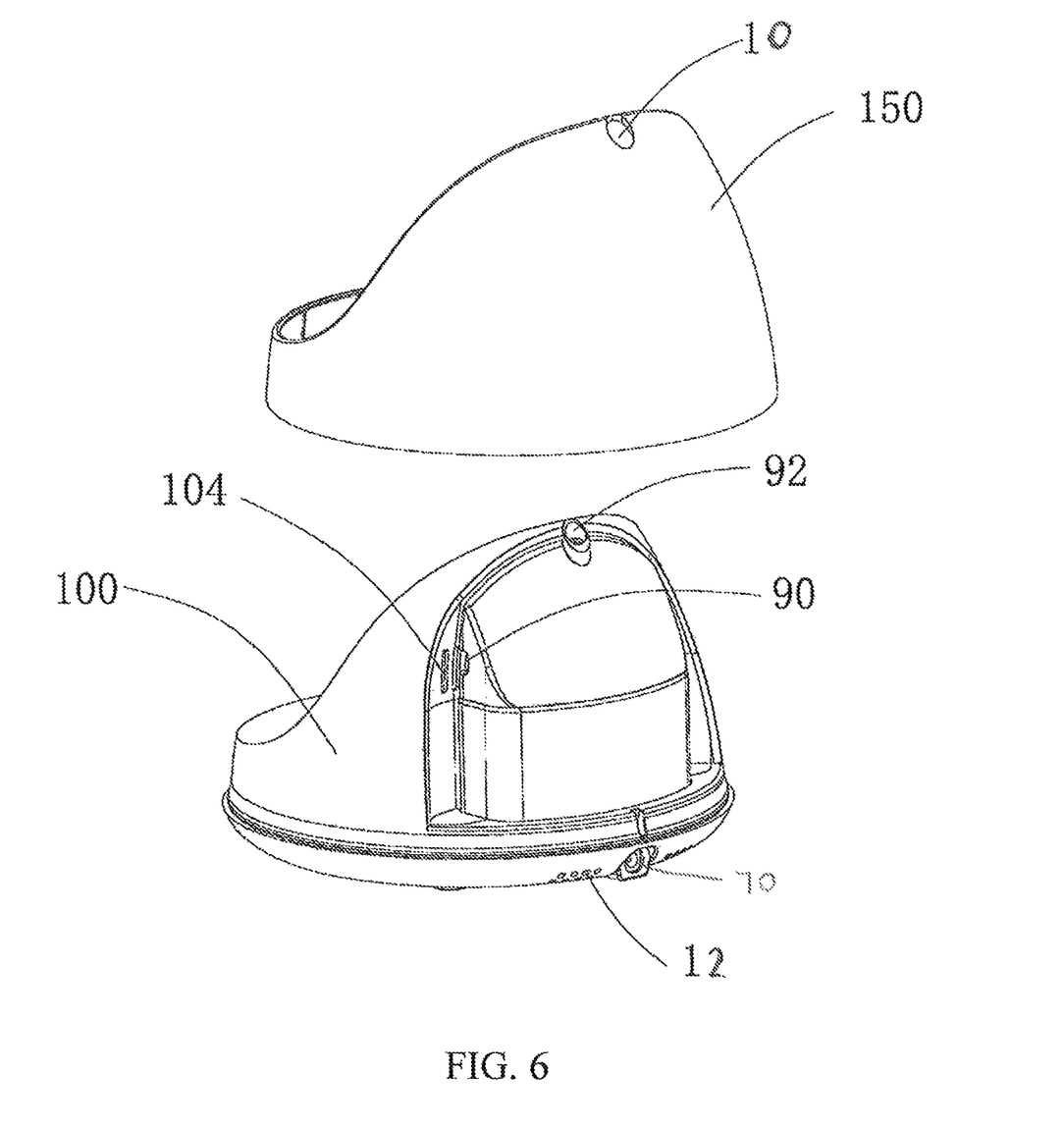
FIG. 6 is another exploded view of the combination salt lamp and aroma/essential oil diffuser of the present invention.
Figure 7:
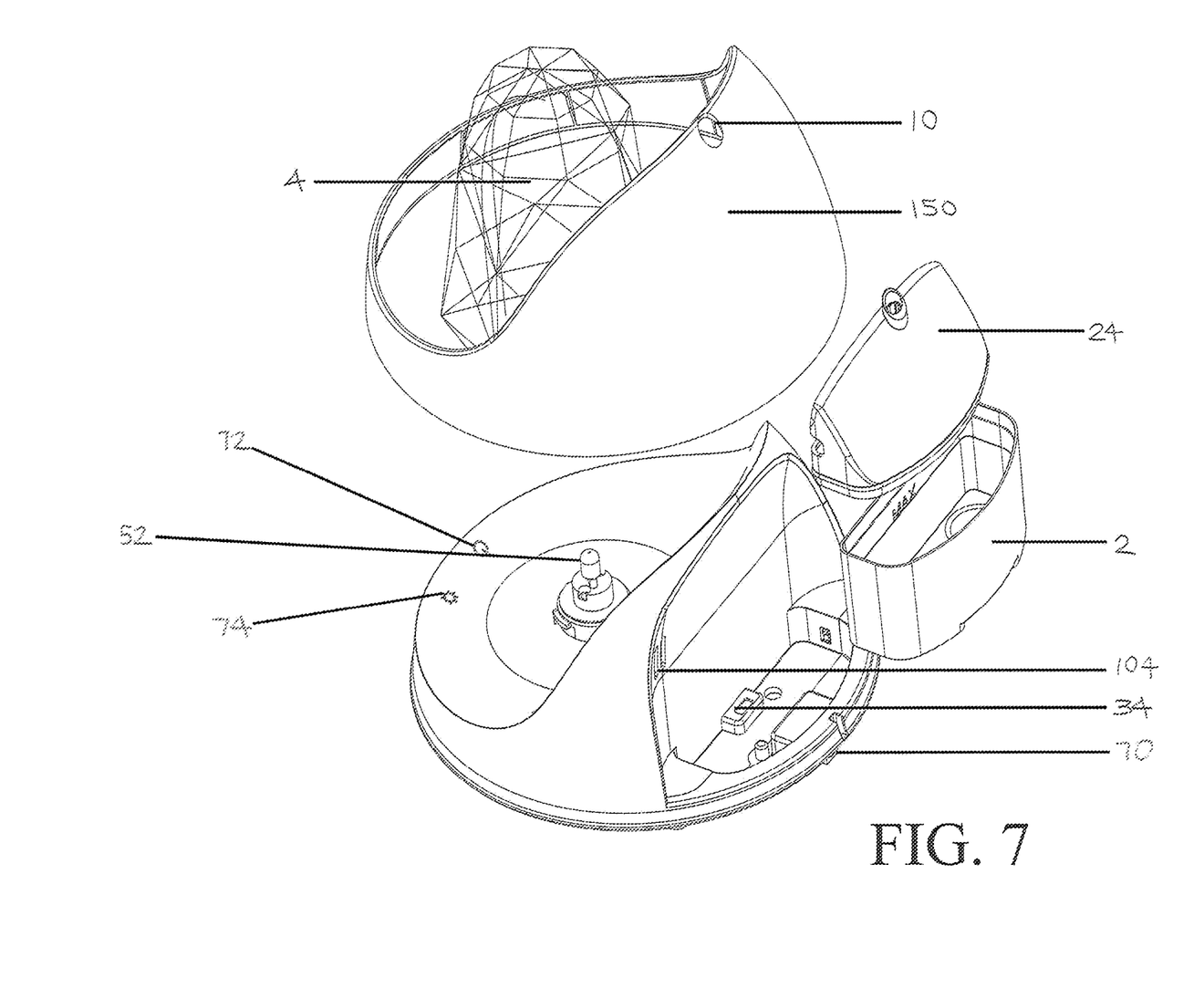
FIG. 7 is an exploded view from a different perspective of the combination salt lamp and aroma/essential oil diffuser of the present invention.
Figure 8:
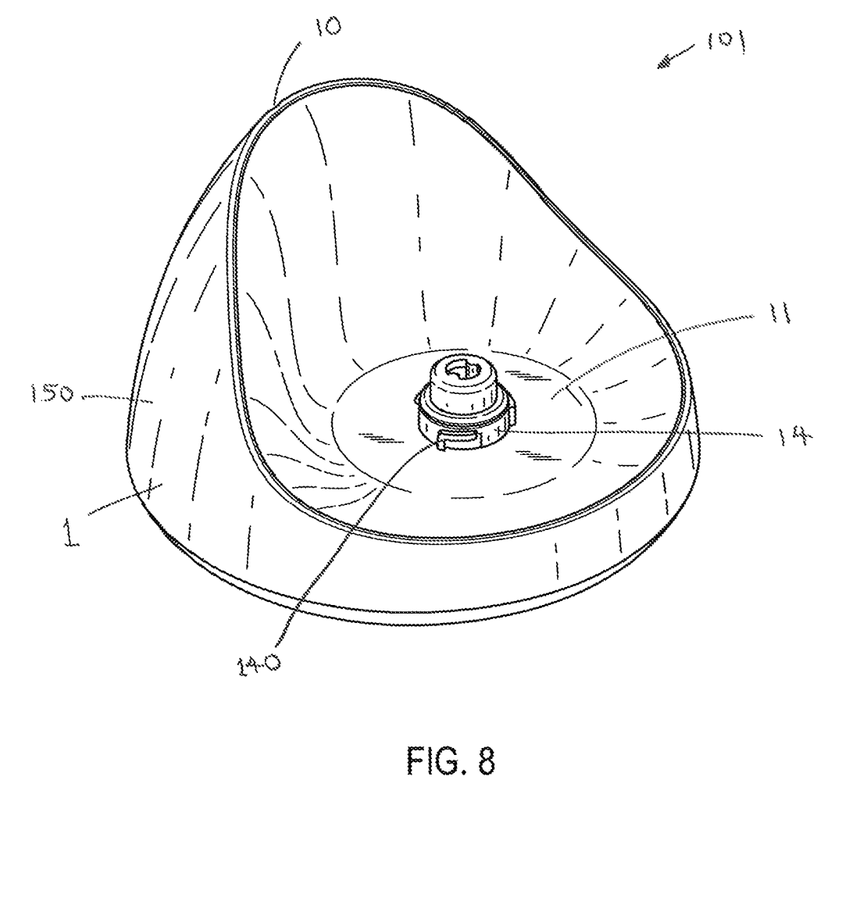
FIG. 8 is a perspective view of the combination salt lamp and aroma/essential oil diffuser of the present invention without the salt crystal mineral.

The water tank 2 is positioned within the housing 1 to store liquid to be nebulized. The water tank 2 can be removably placed in the concave groove 102 to allow easy cleaning of the water tank 2. The water tank 2 includes a water container 20 for holding a liquid to be nebulized, a water tank base 22 for isolating the electrical components, and an inner cover 24 for the water container 20. The water container 20 is located on top of the water tank base 22 and the inner cover 24 is positioned to enclose the water container 20. The inner cover 24 has a second air outlet 92 at the top and a second air inlet 90 on the side, which is positioned adjacent a third air outlet 104 on the top cover 100 of the housing 1. The second air outlet 92 is connected to the mist outlet 10. The outside cover 150 encloses and conceals a portion of the top cover 100 and the water tank 2.

Nebulizing assembly 3 is positioned within the water tank 2 to nebulize the liquid in the water tank 2. The liquid can be water with essential oils added. The nebulizer function of this invention increases the humidity around the diffuser 101 enabling the salt crystal mineral 4 to have enough nebulized water molecules to effectively and continuously produce negative ions to refresh the ambient air. The nebulizer assembly 3 includes an ultrasonic element 30, male contact elements 32, and female contact board 34. The ultrasonic element 30 is placed in the water tank base 22 and through the bottom of the water container 20 such that it is in contact with the liquid stored therein. The male contact 32 is electrically connected to the ultrasonic element 30 and positioned to be protruding from the bottom of the water tank base 22. The female contact board 34 is inside the chamber 112 and accessible from the top cover 100 adjacent the concave groove 102. When the water tank 2 is placed in the concave groove 102, the male contact 32 touches the female contact board 34 to complete the electrical circuit. When the water tank 2 needs to be cleaned, one can simply lift and remove the entire water tank 2 from the concave groove 102 without the need to unplug the diffuser 101. This also simplifies the reassembly by sliding/fitting the water tank 2 into the concave groove 102 for electrical reconnection.

Figure 3:
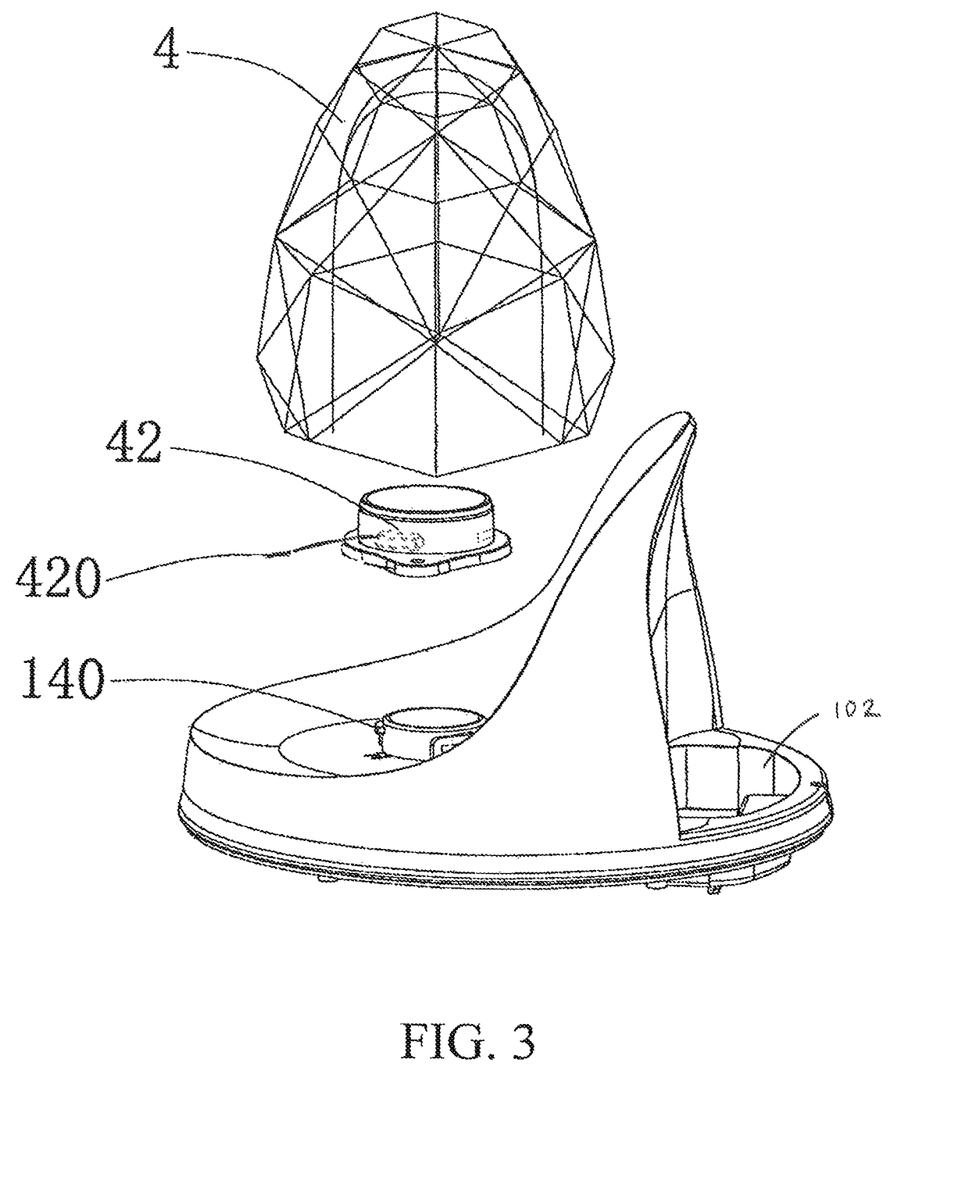
FIG. 3 is an exploded view of the mounting fixture of the salt crystal mineral.

Salt crystal mineral 4 fits on the mounting base 14 at the open space 11 of the housing 1. Salt crystal mineral 4 has an opening 41 defining a hollow cavity 40. The opening 41 fits over the mounting base 14. At the opening 41 is a mounting fixture 42 that is fixedly connected to the salt crystal mineral 4 by any fastening means known to one skilled in the art, such as friction hold, adhesive, or screws through the holes on the mounting fixtures 42. The mounting fixture 42 allows the salt crystal mineral 4 to be removably connected to the mounting base 14 of the housing 1. The mounting fixture 42 has a locking thread or a plurality of notches 420 in its inner wall that correspondingly engages the locking groove 140 on the outer wall of the mounting base 14. Locking thread 420 and locking groove 140 allow the mounting fixture 42 to firmly connect to the diffuser housing 1. This way, it is easy to take apart the salt crystal mineral 4 to clean or to replace it.

The salt crystal mineral 4 may be cone shaped or generally cylindrical shaped with the top of the salt crystal mineral 4 the same or close to the same height as the mist outlet 10.

This way, some of the mist releasing from the mist outlet 10 will fall by gravity onto the salt crystal mineral 4, and negative ions will be produced by the salt crystal mineral 4. By adding humidity, it improves the production of negative ions thus refreshes the ambient air. The ideal salt crystal mineral 4 for the diffuser 101 is the Himalayan salt crystal because it contains at least 98% sodium chloride, with other elements including iron, calcium, potassium, magnesium, phosphorus, zinc, and many other minerals that are beneficial to the body.

Heating assembly 5 includes a heating element 50 that extends into the open space 11 through the mounting base 14 from the chamber 112 to be positioned within the hollow cavity 40 of the salt crystal mineral 4. The heating element 50 can be a heating coil or heating plate. The heating element 50 can also be a halogen bulb 52 that provides not only heat, but also light such that the salt crystal mineral 4 glows. The light from the halogen bulb 52 filters through the translucent salt crystal mineral 4 to give a warm glow to create a nice atmosphere or act as a night light. The halogen bulb 52 may have several settings for different levels of brightness. A LED light 8 is optionally provided adjacent the heating element 50 inside the hollow cavity 40 of the salter crystal mineral 4, if the halogen bulb 52 is not used. The LED light 8 is electrically connected to the power assembly 7 and provides the same effect as the halogen bulb 52.

Fan assembly 6 blows the mist from the nebulized liquid through the housing 1 to the mist outlet 10. When the diffuser 101 is powered on, the fan assembly 6 draws outside air through the air inlet 12 into the chamber 112, which then exits at third air outlet 104, and enters the second air inlet 90 inside the inner cover 24. The air flow from inside the inner cover 24 carries the nebulized mist created inside water tank 2 out to the second air outlet 92 to mist outlet 10 to the surrounding air.

Power assembly 7 provides electrical power to the ultrasonic nebulizing assembly 3, the heating assembly 5, and the fan assembly 6. The power assembly 7 includes a DC inlet 70, an on/off switch 72 and a controller 74 that can control the intensity of the heating assembly 5 (such as a dimmer to the halogen bulb 52 for different levels of brightness).

Figure 9:
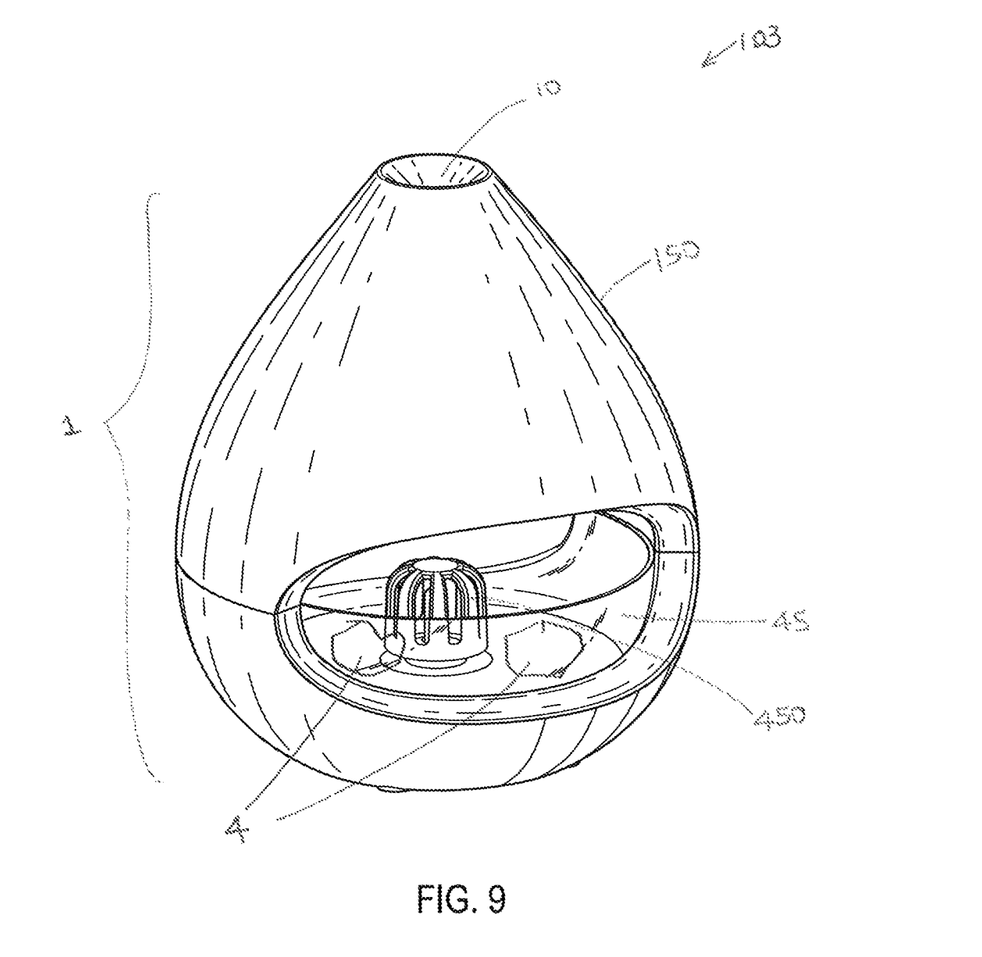
FIG. 9 is a perspective view of a second embodiment of the combination salt lamp and aroma/essential oil diffuser of the present invention.
Figure 10:
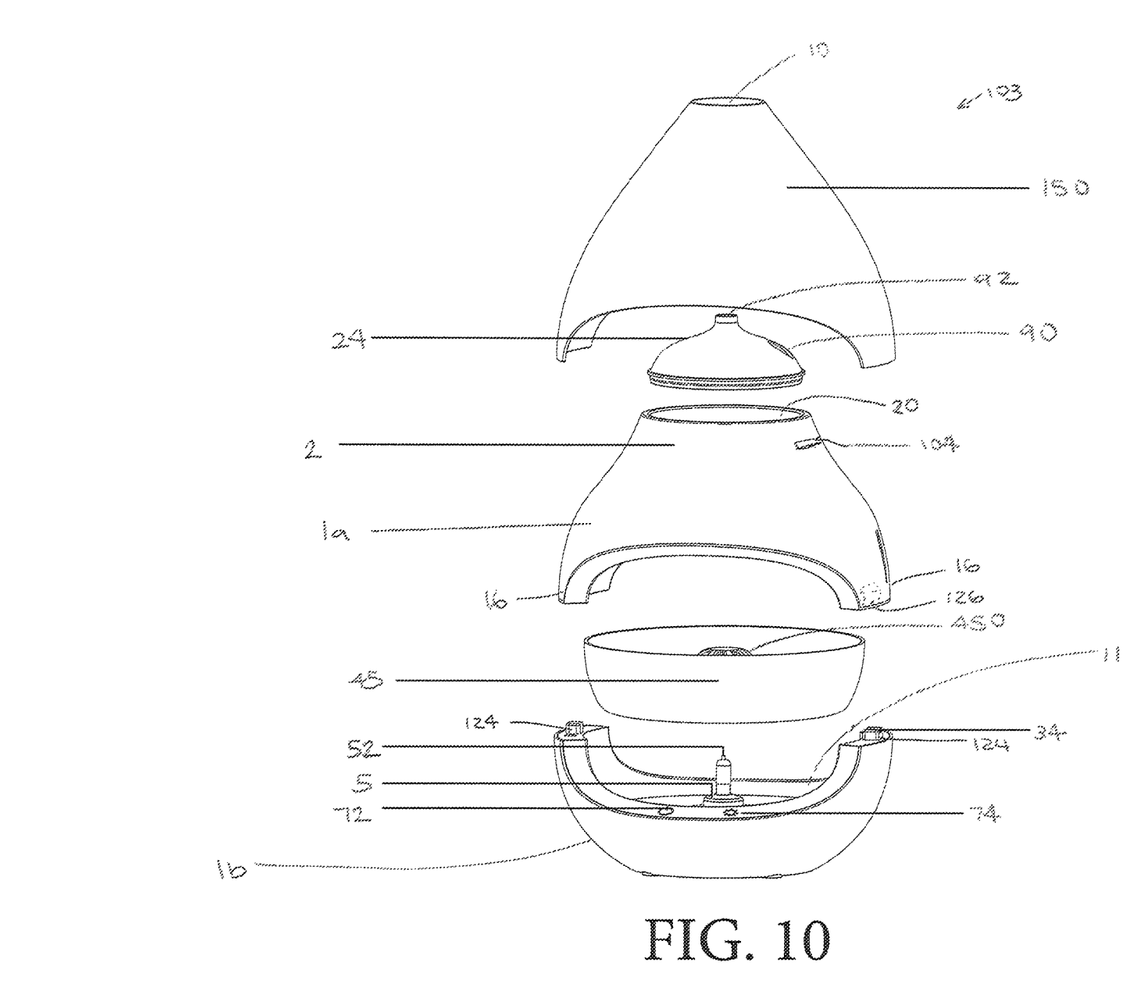
FIG. 10 is a partially exploded view of FIG. 9.
Figure 11:
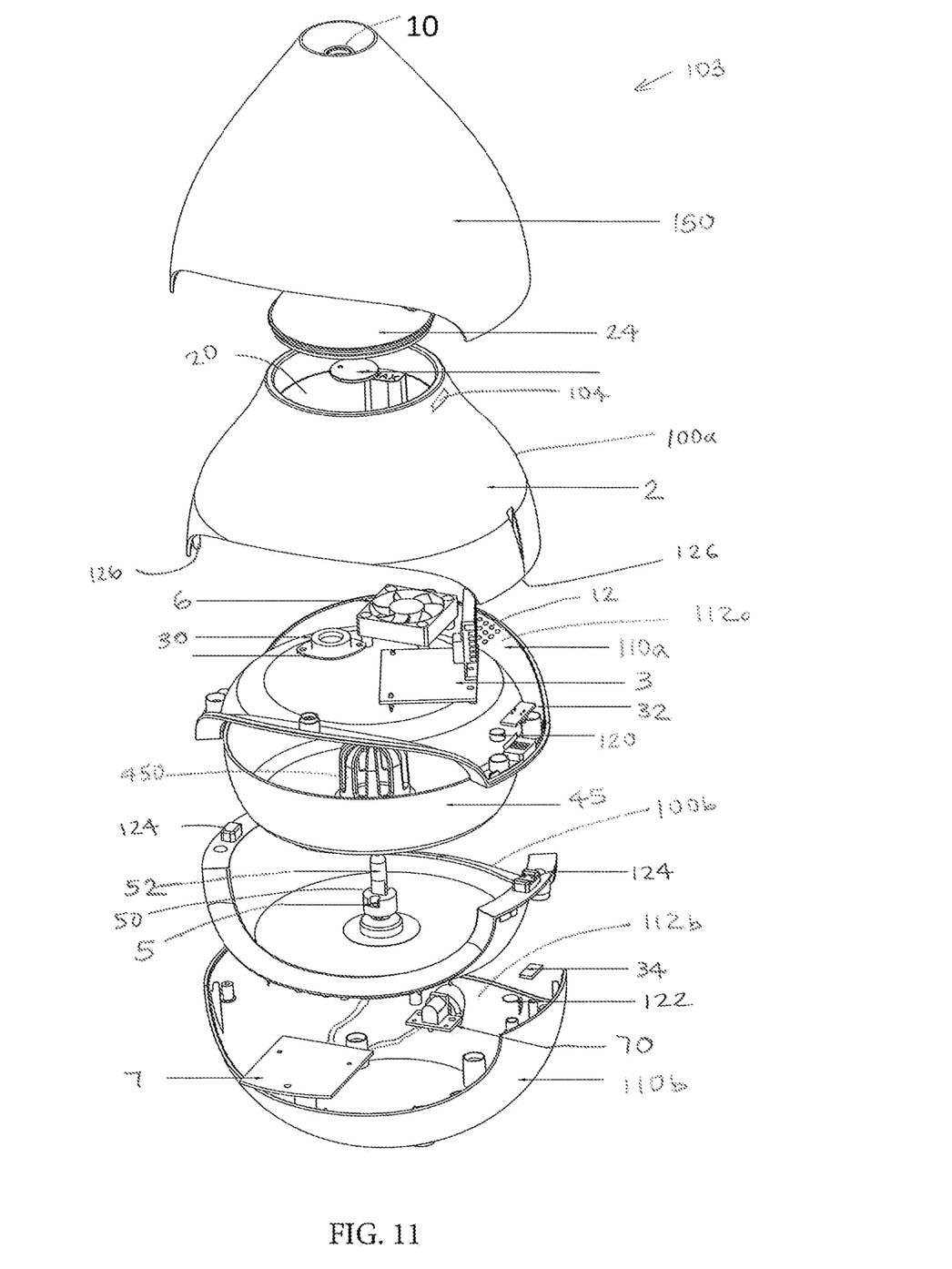
FIG. 11 is another partially exploded view of FIG. 9.

FIGS. 9 to 11 is a second embodiment of the combination salt lamp and aroma/essential oil diffuser 103 of the present invention. The combination salt lamp and aroma/essential oil diffuser 103 is similar to the combination salt lamp and aroma/essential oil diffuser 101 shown in FIGS. 1 to 8, and the same reference numbers are used to indicate the same components.

The housing 1 of the diffuser 103 includes upper housing 1a and lower housing 1b. The upper housing 1a is removably connected to the lower housing 1b. The mist outlet 10 is in the upper housing 1a. The open space 11 is defined between the upper and lower housings 1a and 1b. Each of the upper and lower housings 1a and 1b has a corresponding top cover 100a and 100b and a bottom cover 110a and 110b, which are respectively joined together to form upper and lower chambers 112a and 112b, respectively. The fan assembly 6 and the nebulizing assembly 3 are both placed in upper chamber 112a. The power assembly 7 is placed in lower chamber 112b. On the bottom cover 110a of upper housing 1a is a plurality of air inlets 12 for the intake of air from outside the diffuser 103. The upper housing 1a has a pair of legs 16 extending downwardly to engage and connect to the lower housing 1b. At each leg 16 is an indentation 126 that is correspondingly sized to mate with a raised platform 124 on the top cover 100b of the lower housing 1b. The two sets of indentations 126 and raised platforms 124 ensure that the upper housing 1a is correctly positioned on top of the lower housing 1b. To further assist in the correct positioning of the upper housing 1a to the lower housing 1b is a magnet 120 adjacent an indentation 126 and a corresponding metal plate 122 adjacent a raised platform 124.

The water tank 2 is part of and integral with the upper housing 1a, with the water container 20 defined by a depression formed on the top cover 100a of the upper housing 1a. Since the upper housing 1a is removably connected to the lower housing 1b, the water tank 2 can be removed to allow easy cleaning of the water tank 2. An inner cover 24 encloses the water container 20. The inner cover 24 has a second air outlet 92 at the top and a second air inlet 90 on the side, which may be rotatably positioned to be adjacent a third air outlet 104 on the top cover 100a of the upper housing 1a. The second air outlet 92 is connected to/in communication with the mist outlet 10. The outside cover 150 encloses and conceals the upper housing 1a and inner cover 24.

Nebulizing assembly 3 is positioned insider the water tank 2 (i.e. upper housing 1a). The nebulizing element 30 is placed in the water tank 2 and through the bottom of the water container 20 such that it is in contact with the liquid stored therein. The male contact 32 is electrically connected to the nebulizing element 30 and protrudingly extends from the bottom cover 110a of the upper housing 1a at one of the two indentations 126. The female contact board 34 is inside the lower housing 1b and accessible from the top cover 100b of the lower housing 1b at one of the two raised platforms 124. When the upper housing 1a is positioned over the lower housing 1b, the male contacts 32 touch the female contact board 34 to complete the electrical circuit. When the water tank 2 needs to be cleaned, one can simply lift and remove the upper housing 1a from the lower housing 1b without the need to unplug the diffuser 103.

A bowl 45 is provided in the open space 11 to receive a plurality of salt crystal minerals 4. Instead of using a single salt crystal mineral 4 shown in FIG. 1 for the diffuser 101, the diffuser 102 uses a plurality of salt crystal mineral 4. The bowl 45 has a central, slotted, protrusion 450 to receive and accommodate the heating assembly 5. The plurality of salt crystal mineral s4 can be piled up to cover the protrusion 450 without interfering with the heating assembly 5. The bowl is preferably transparent or translucent. The use of a plurality of smaller salt crystal minerals 4 facilitates the cleaning and/or replacement of the salt crystal minerals 4. Similar to the diffuser 101, the mist that is released from the mist outlet 10 will fall by gravity over the outer cover 150 towards the salt crystal mineral 4 in the open space 11. The increase in humidity improves the production of negative ions and thus refreshes the ambient air.

The heating assembly 5 is located at the lower housing 1b, in the open space 11. The heating element 50 is a halogen bulb 52. The halogen bulb 52 produces heat and light, through the protrusion 450 of the bowl 45 to heat and light up the plurality of salt crystal minerals 4 in the bowl 45.

Fan assembly 6 blows the mist from the nebulized liquid through the upper housing 1a to the mist outlet 10. When the diffuser 103 is powered on, the fan assembly 6 draws outside air through the air inlet 12 on the bottom cover 110a of the upper housing 1a, which then exits at third air outlet 104, and enters through the second air inlet 90 inside the inner cover 24. The air flow from inside the inner cover 24 carries the nebulized mist created inside water tank 2 out to the second air outlet 92 to mist outlet 10 to the surrounding air.

Power assembly 7 provides power to the ultrasonic nebulizing assembly 3 and the fan assembly 6 in the upper chamber 112a via the female contact board 34 and the male contacts 32, and directly to the heating assembly 5 in the lower chamber 112b through a hard wire. The power assembly 7 includes a DC inlet 70, an on/off switch 72, and a controller 74 that can control the intensity of halogen bulb 52 of the heating assembly 5 with a dimmer.

The features of the invention illustrated and described herein are the preferred embodiments. Therefore, it is understood that the specification is intended to cover unforeseeable embodiments with insubstantial differences that are within the spirit of the specification.

What we claim is:

1. A combination salt lamp and aroma/essential oil diffuser for nebulizing a liquid into mist comprises:
    a lower housing;
    an upper housing above said lower housing having a first outlet for the nebulized mist to exit;
    an open space defined between said upper housing and said lower housing;
    a water tank inside said upper housing for storing the liquid to be nebulized;
    an ultrasonic nebulizing assembly inside said upper housing within said water tank to nebulize the liquid in said water tank;
    a salt crystal mineral in said open space;
    a heating assembly having a heating element extending from said lower housing into said open space adjacent said salt crystal mineral;
    a fan assembly inside said upper housing to aid in the dispersing of the mist from said water tank to said first outlet;
    a power assembly inside said lower housing providing power to said ultrasonic nebulizing assembly, said heating assembly, and said fan assembly;
    at least one first electrical contact at said upper housing to provide power from said power assembly to said ultrasonic nebulizing assembly and said fan assembly;
    at least one second electrical contact at said lower housing to provide power from said power assembly to said ultrasonic nebulizing assembly and said fan assembly;
    wherein said upper housing is removably connected to said lower housing, such that upon connection of said upper housing to said lower housing, said at least one first electrical contact is electrically connected to said at least one second electrical contact to provide power to said ultrasonic nebulizing assembly and said fan assembly, and upon disconnection of said upper housing from said lower housing, power to said ultrasonic nebulizing assembly and said fan assembly is automatically disconnected.

2. The combination salt lamp and aroma/essential oil diffuser of claim 1, wherein said heating element is a halogen bulb.

3. The combination salt lamp and aroma/essential oil diffuser of claim 1, wherein said water tank is removable from inside said housing.

4. The combination salt lamp and aroma/essential oil diffuser of claim 1 wherein said upper and lower housings each comprises a top cover and a bottom cover, said top and bottom covers of said upper housing join together to form upper chambers, said top and bottom covers of said lower housing join together to form lower chamber, wherein said fan assembly and ultrasonic nebulizing assembly are located in said upper chamber, and said power assembly is located in said lower chamber.

5. The combination salt lamp and aroma/essential oil diffuser of claim 4 wherein said upper housing has a pair of legs extending downwardly to connect to said lower housing.

6. The combination salt lamp and aroma/essential oil diffuser of claim 5, wherein said top cover of said lower housing having at least one raised platform, and at least one of said pair of legs has an indentation that is correspondingly sized to mate with said raised platform, said at least one first electrical contact is located at said indentation and said at least one second electrical contact is located at said at least one raised platform.

7. The combination salt lamp and aroma/essential oil diffuser of claim 4, wherein said water tank is defined by a depression on said top cover of said upper housing.

8. The combination salt lamp and aroma/essential oil diffuser of claim 4, wherein said ultrasonic nebulizing assembly comprises: an ultrasonic element placed in said water tank and through said water tank to be in contact with the liquid stored in said water tank; male contacts electrically connected to said ultrasonic element and positioned to be protruding from said bottom cover of said upper housing; and a female contact board on said top cover of said lower housing.

9. The combination salt lamp and aroma/essential oil diffuser of claim 1 further comprising a bowl in said open space for receiving said salt crystal mineral.

10. The combination salt lamp and aroma/essential oil diffuser of claim 9 wherein said bowl having a central, slotted protrusion for receiving said heating element therein.

* * * * *